United States Patent [19]

Diel

[11] 4,247,691
[45] Jan. 27, 1981

[54] 1,2,4-BENZOTRIAZINE-1,4-DI-N-OXIDES

[75] Inventor: Peter J. Diel, Muttenz, Switzerland

[73] Assignee: Ciba-Geigy Corporation, Ardsley, N.Y.

[21] Appl. No.: 878,636

[22] Filed: Feb. 17, 1978

[30] Foreign Application Priority Data

Feb. 22, 1977 [CH] Switzerland ........................ 2184/77

[51] Int. Cl.³ .......................................... C07D 253/08
[52] U.S. Cl. .................................. 544/183; 424/249; 542/421
[58] Field of Search .................. 544/183; 424/249

[56] References Cited

U.S. PATENT DOCUMENTS

| | | | |
|---|---|---|---|
| 3,957,779 | 5/1976 | Seng et al. | 544/183 |
| 3,991,189 | 11/1976 | Seng et al. | 544/183 |
| 4,079,062 | 3/1978 | Van Reet et al. | 260/308 |
| 4,160,833 | 7/1979 | Diel | 544/183 |

FOREIGN PATENT DOCUMENTS

| | | |
|---|---|---|
| 2204574 | 8/1973 | Fed. Rep. of Germany ............ 544/183 |
| 2255825 | 5/1974 | Fed. Rep. of Germany ............ 544/183 |
| 2255947 | 5/1974 | Fed. Rep. of Germany ............ 544/183 |
| 2404375 | 8/1974 | Fed. Rep. of Germany ............ 544/183 |

*Primary Examiner*—John M. Ford

*Attorney, Agent, or Firm*—Frederick H. Rabin

[57] ABSTRACT

This invention concerns novel 1,2,4-benzotriazine-di-N-oxide derivatives having the general formula

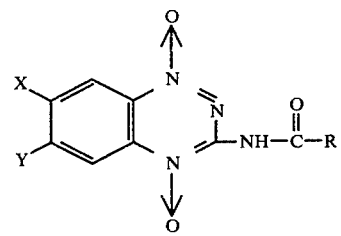

wherein
X and Y, each independently of the other, represent hydrogen, halogen, $C_1$–$C_4$alkyl, $C_1$–$C_4$alkoxy, and
R—represents a $C_2$–$C_8$alkenyl radical which is unsubstituted or substituted by $C_1$–$C_4$alkyl or halogen, or represents an aralkenyl radical containing 2 to 8 carbon atoms in the alkenyl moiety, compositions containing the novel compounds and the use of the novel compounds for growth-promoting of domestic animals and productive livestock and for controlling diseases in the field of veterinary medicine.

3 Claims, No Drawings

1,2,4-BENZOTRIAZINE-1,4-DI-N-OXIDES

The present invention relates to novel 1,2,4-benzotriazine-di-N-oxide derivatives, processes for the production of these compounds as well as compositions containing these compounds as active component, and to the use of these compounds.

The compounds of the invention are distinguished by growth-promoting properties when administered to domestic animals and productive livestock. In addition, they possess microbicidal activity and are suitable for controlling diseases in the field of veterinary medicine.

The novel 1,2,4-benzotriazine-di-N-oxide derivatives have the general formula I

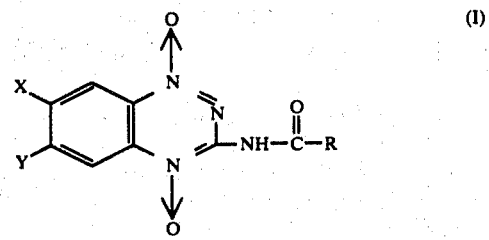

wherein
X and Y, each independently of the other, represent hydrogen, halogen, $C_1$–$C_4$alkyl, $C_1$–$C_4$alkoxy, and
R—represents a $C_2$–$C_8$alkenyl radical which is unsubstituted or substituted by $C_1$–$C_4$alkyl or halogen, or represents an aralkenyl radical containing 1 to 8 carbon atoms in the alkenyl moiety.

Possible alkyl radicals are methyl, ethyl as well as the isomers of propyl and butyl, and possible alkoxy radicals are methoxy, ethoxy as well as the isomers of propoxy and butoxy. By halogenalkyl radicals are meant alkyl radicals which are mono- or polysubstituted by fluorine, chlorine, bromine or iodine, for example trifluoromethyl. Halogen denotes fluorine, chlorine, bromine or iodine, and is preferably chlorine or bromine. Preferred alkenyl radicals are those containing 2 to 5 carbon atoms, including for example ethenyl, propenyl or allyl. Aryl on which the aralkenyl radicals are based is in particular phenyl.

The intensive production pursued for economic reasons in modern farming in the rearing and fattening of productive livestock carries with it an increased danger of infection as a consequence of the mass stock rearing. The occurrence of infectious diseases can result in these circumstances in a drastic diminution of the useful performance and often even in the death of the affected animals, which in general is allied to substantial economic losses. For this reason intensive efforts are being made successfully to prevent such damage caused by agricultural production by providing suitable active compounds and methods of using them for controlling and preventing these diseases. In addition, it is especially important to improve the growth of healthy domestic animals and productive livestock. This growth can be effected by chemical compounds which are suitable for the purpose. In view of the worldwide shortage of food for human nutrition, especially of animal protein, and also of animal feedstuffs, an economic importance which is not to be underestimated attaches to this aspect.

There has been no lack of attempts to prepare and make available compounds as active substances for the above mentioned purposes. Benzotriazine-di-N-oxide compounds of similar structure are cited in German Offenlegungsschriften Nos. 2,204,574, 2,255,825 and 2,255,947. In actual practice, however, the compounds prepared hitherto have not been able to fulfill satisfactorily the demands made of them.

The benzotriazine-di-N-oxide derivatives of the formula I are distinguished by their good action in promoting the growth of domestic animals and productive livestock and in improving the feed utilisation capacity by the animals.

The compounds of the formula I have in addition good microbicidal action against pathogenic micro-organisms. They can therefore be used with advantage in veterinary medicine for controlling pathogens on and in animals, especially against infections of the digestive and respiratory tract and of the urinary tract.

Depending on the end-use, the active compounds of the formula I can be administered to the animals in the form of solutions, emulsions, suspensions, powders, pellets, boluses and capsules perorally, via the abomasum or by injection direct, both in individual and repeated doses. The active compounds or mixtures containing them can also however be added to the feed or drink or be contained in a premix.

For feeding purposes, the active compounds can be employed either in the form of a concentrated premix for mixing with a standard feed or as a compound feed mix which can be fed direct to the animals.

A suitable premix is for example a mixture of the active compound of the formula I with kaolin, lime, alumina, ground mussel shells, bolus alba, aerosil, starch or lactose.

To produce a feed mix which contains the active component in a concentration between 1 and 500 ppm, the necessary amounts of the premix are thoroughly mixed with the corresponding amount of a commercially available standard feed for the respective species of animal.

Furthermore, the active compounds of the invention for controlling pathogenic micro-organisms in veterinary medicine and for achieving a growth-promoting effect in domestic animals and productive livestock can additionally be combined with suitable substances which aid the intended action.

The compounds of the formula I are obtained in a manner known per se by reacting compounds of the formula II

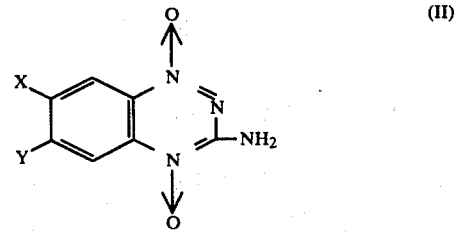

wherein X and Y are as defined in formula I, either
(a) with a carboxylic acid halide of the formula III R—CO—Hal     (III)

or (b) with a carboxylic acid anhydride of the formula IV $$(R-CO)_2O \quad (IV)$$

or (c) with a mixed carboxylic acid anhydride of the formula V $$R-\underset{\underset{O}{\|}}{C}-O-\underset{\underset{O}{\|}}{C}-CF_3 \quad (V)$$

wherein R is as defined in formula I.

The reaction with the carboxylic acid halide takes place in the presence of a base either in an organic solvent or diluent or in a mixture consisting of an organic solvent or diluent and water. If a tertiary amine is used as base, it can simultaneously act as solvent. Preferred carboxylic acid halides are the chlorides and bromides (Houben-Weyl, Vol. 11/2, pp. 10–14).

The reaction with the carboxylic acid anhydride on the other hand is carried out either in an organic solvent or diluent or in a carboxylic acid from which the anhydride is derived. (Houben-Weyl, Vol. 11/2, pp. 16–19, 31–34).

The reaction temperatures in the process for obtaining the compounds of the formula I are between 0° and 10° C.

Suitable acid acceptors are for example inorganic bases; the hydroxides or carbonates of alkali metals or alkaline earth metals are preferred. However, organic bases, such as tertiary amines, for example pyridine or pyridine bases, trialkylamines, such as triethylamine, can also be used.

Suitable solvents and/or diluents for the reactions are those which are inert to the reactants, such as aromatic hydrocarbons, for example benzene, toluene, xylenes; halogenated hydrocarbons, such as chlorobenzene, chloroform, carbon tetrachloride; ethers and ethereal compounds, such as dialkyl ethers and cyclic ethers, for example dioxane; ketones, such as acetone, methyl ethyl ketone; and mixtures of such solvents with each other or with water (two-phase system), especially a mixture of methyl ethyl ketone and water.

The starting materials of the formula II are known and are obtained by the processes described by Arndt and Eistert in Chem. Ber. 46 (1913), 3522, Robinson and Schofield in J. Chem. Soc. 1957, 3186–94, Mason and Tennant in J. Chem. Soc (B), 1970, 911–916, and Ley and Seng in Angew. Chem. 84 (1972), 1061.

EXAMPLE 1

3-Crotonylamino-7-methoxy-1,2,4-benztriazine-1,4-di-N-oxide 10.4 g (0.05 mole) of 3-amino-7-methoxy-1,2,4-benztriazine-1,4-di-N-oxide are heated together with 75 g of crotonic acid to 70° C. and treated, with stirring, with 8.5 g (0.06 mole) of crotonic anhydride. The mixture is stirred for 2 hours at 85° C., then cooled to 75° C., diluted with 50 ml of glacial acetic acid and filtered. The filter residue is washed firstly with dioxane and then with ethanol and dried.

Yield: 11.3 g of yellow crystals (81.5%). Melting Point: 217°–219° C., with decomp.

EXAMPLE 2

3-Cinnamoylamino-7-methoxy-1,2,4-benztriazine-1,4-di-N-oxide 10.4 g (0.05 mole) of 3-amino-7-methoxy-1,2,4-benztriazine-1,4-di-N-oxide are suspended in 300 ml of dioxane. The suspension is heated to 60° C., then 6.5 ml (0.075 mole) of pyridine are added all at once, followed by the dropwise addition of 12.5 g (0.075 mole) of cinnamyl chloride in 50 ml of dioxane. The reaction mixture is stirred for 6 hours at 60° C., then filtered with suction at room temperature. The filter cake is washed with dioxane and dried in vacuo at 50° C. Yield: 21.5 g of yellow crystals (85%). Melting point: 215°–217° C., with decomp.

EXAMPLE 3

3-Crotonylamino-7-methyl-1,2,4-benztriazine-1,4-di-N-oxide 19.2 g (0.1 mole) of 3-amino-7-methyl-1,2,4-benztriazine-1,4-di-N-oxide are suspended in 250 ml of toluene. Then 17 g (0.11 mole) of crotonic anhydride are added and the reaction mixture is stirred for 6 hours at reflux. The yellow precipitate is filtered off at room temperature, washed with toluene and dried in vacuo.

Yield: 11.2 g (68%). Melting point: 202°–204° C., with decomp.

The following compounds can be prepared in the manner described in the preceding Examples:

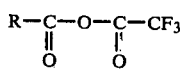

| X | Y | R | Physical data |
|---|---|---|---|
| H | H | —CH=CH—CH₃ | m.p. 213–215° C. |
| Cl | H | —CH=CH—CH₃ | m.p. 217–219° C. |
| H | H | —CH=CH—C₆H₅ | m.p. 194° C. (decomp.) |
| CH₃ | H | —CH=CH—C₆H₅ | m.p. 235–237° C. |
| Cl | H | —CH=CH—C₆H₅ | m.p. 208° C. |
| CH₃ | H | —CH=CH—CH₂—CH₂—CH₃ | m.p. 193–195° C. |

Feed additive

The following premixes were prepared for the production of 6000 parts by weight with (a) 25 ppm, (b) 50 ppm, (c) 200 ppm, and (d) 400 ppm:

(a) 0.15 parts—of one of the compounds of formula I
  49.85 parts—of bolus alba
  150.00 parts—of standard feed for poultry, swine or ruminants.

(b) 0.30 parts—of one of the compounds of formula I
  44.70 parts—of bolus alba
  5.0 parts—of silicic acid
  150.0 parts—of standard feed for poultry, swine or ruminants.

(c) 1.2 parts of one of the compounds of formula I 43.8 parts—of bolus alba
5.0 parts—of silicic acid
150.0 parts—of standard feed for poultry, swine or ruminants.
(d) 2.4 parts—of one of the compounds of formula I
47.6 parts—of bolus alba
150.0 parts—of standard feed for poultry, swine or ruminents.

The active substances are either mixed direct with the carriers or applied in the form of a solution thereto. The mixture is then ground to the desired particle size of e.g. 5 to 10μ. These premixes are mixed with 5800 parts by weight of standard feed or processed to 6000 parts by weight of preprepared drink. In addition, these premixes can be made into pellets together with 5800 parts by weight of standard feed (feed pellets).

The above feed mixes exhibit a marked growth-promoting action in comparison to control animals which are fed with the correspondingly identical feed mixes and formulations without the addition of active substance.

What is claimed is:

1. A compound of the formula I

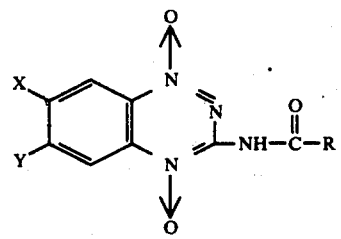

wherein
X and Y, each independently of the other, represent hydrogen, halogen, $C_1$-$C_4$ alkyl, $C_1$-$C_4$ alkoxy, and
R represents $C_2$-$C_8$ alkenyl which is unsubstituted or substituted by $C_1$-$C_4$ alkyl or halogen.

2. 3-Crotonylamino-7-methyl-1,2,4-benztriazine-1,4-di-N-oxide according to claim 1.

3. 3-Crotonylamino-1,2,4-benztriazine-1,4-di-N-oxide according to claim 1.